(12) United States Patent
Hobro et al.

(10) Patent No.: US 11,944,732 B2
(45) Date of Patent: Apr. 2, 2024

(54) DIALYSIS SYSTEM HAVING LOCALIZED DISINFECTION

(71) Applicant: GAMBRO LUNDIA AB, Lund (SE)

(72) Inventors: Sture Hobro, Lund (SE); Helena Jeppsson, Hörby (SE); Björn Ericson, Lund (SE)

(73) Assignee: Gambro Lundia AB, Lund (SE)

( * ) Notice: Subject to any disclaimer, the term of this patent is extended or adjusted under 35 U.S.C. 154(b) by 853 days.

(21) Appl. No.: 16/980,129

(22) PCT Filed: Mar. 7, 2019

(86) PCT No.: PCT/EP2019/055662
§ 371 (c)(1),
(2) Date: Sep. 11, 2020

(87) PCT Pub. No.: WO2019/175005
PCT Pub. Date: Sep. 19, 2019

(65) Prior Publication Data
US 2020/0405935 A1   Dec. 31, 2020

(30) Foreign Application Priority Data

Mar. 14, 2018  (SE) .................................. 1850283-1

(51) Int. Cl.
*A61M 1/16* (2006.01)
*A61L 2/18* (2006.01)
(Continued)

(52) U.S. Cl.
CPC .............. *A61M 1/169* (2013.01); *A61L 2/18* (2013.01); *A61L 2/24* (2013.01); *A61M 1/1672* (2014.02);
(Continued)

(58) Field of Classification Search
CPC ....... A61M 1/169; A61M 1/1672; A61L 2/18; A61L 2/24; A61L 2101/36; A61L 2202/14; B08B 9/0325; B08B 2209/032
See application file for complete search history.

(56) References Cited

U.S. PATENT DOCUMENTS

| 5,895,578 A | 4/1999 | Simard et al. |
| 6,027,469 A | 2/2000 | Johnson |
(Continued)

FOREIGN PATENT DOCUMENTS

| CN | 101342389 A | 1/2009 |
| CN | 202154894 U | 3/2012 |
(Continued)

OTHER PUBLICATIONS

English Translation of JP 2005500086 A, downloaded from espacenet; (2005).*

(Continued)

*Primary Examiner* — Terry K Cecil
(74) *Attorney, Agent, or Firm* — K&L Gates LLP

(57) ABSTRACT

An extracorporeal therapy system includes: (i) a dialysis fluid circuit including dialysis fluid preparation structure to prepare a dialysis fluid for treatment, the dialysis fluid circuit including a fresh dialysis fluid pump, a used dialysis fluid pump, and at least one filter for purifying the dialysis fluid; (ii) a blood circuit including a blood filter for use during the treatment; (iii) a blood pump operable to pump blood through the blood circuit and blood filter; (iv) a source of disinfecting fluid; and (v) a control unit operable with the dialysis fluid preparation structure and the blood pump, the control unit programmed to cause the disinfecting fluid to be delivered to and located for a duration at an area of the dialysis fluid circuit having the at least one purifying filter, and wherein during the duration the disinfecting fluid is (Continued)

precluded from contacting at least the fresh dialysis fluid pump.

24 Claims, 4 Drawing Sheets

(51) Int. Cl.
    *A61L 2/24*           (2006.01)
    *A61L 101/36*      (2006.01)
    *B08B 9/032*       (2006.01)

(52) U.S. Cl.
    CPC ......... *B08B 9/0325* (2013.01); *A61L 2101/36* (2020.08); *A61L 2202/14* (2013.01); *B08B 2209/032* (2013.01)

(56) References Cited

U.S. PATENT DOCUMENTS

| | | | |
|---|---|---|---|
| 9,440,017 B2 * | 9/2016 | Rohde | .................. A61M 1/287 |
| 2013/0037480 A1 * | 2/2013 | Wilt | .................. A61M 1/3401 |
| | | | 210/321.69 |

FOREIGN PATENT DOCUMENTS

| | | | | |
|---|---|---|---|---|
| CN | 103830756 A | | 6/2014 | |
| JP | 2005500086 A | * | 1/2005 | .......... A61M 1/1685 |
| WO | WO 9015631 | | 12/1990 | |
| WO | WO 9309821 | | 5/1993 | |

OTHER PUBLICATIONS

First Office Action and Search Report, Chinese Patent Application No. 201980019059.6, pp. 1-21, dated Feb. 18, 2023, dated Mar. 2, 2023.

International Search Report; International Application No. PCT/EP2019/055662 dated May 27, 2019; 4 Pages.

Written Opinion of the International Searching Authority; International Application No. PCT/EP2019/055662 dated May 27, 2019; 6 Pages.

B Canaud1 et al, "Nephrology Dialysis Transplantation On-line haemodiafiltration. Safety and efficacy in long-term clinical practice", Jan. 1, 2000 (Jan. 1, 2000), p. 60-67, Retrieved from the Internet: URL:https://www.researchgate.net/publication/12579423_On-line_haemodiafiltration_Safety_and_efficacy_in_long-term_clinical_practice *.

* cited by examiner

DIALYSIS SYSTEM HAVING LOCALIZED DISINFECTION

PRIORITY CLAIM

The present application is a National Phase of International Application No. PCT/EP2019/055662, filed Mar. 7, 2019, which claims priority to Swedish Application No. 1850283-1, filed Mar. 14, 2018, the entire contents of each of which are incorporated herein by reference and relied upon.

BACKGROUND

The present disclosure relates generally to medical delivery. More specifically, the present disclosure relates to the disinfection of extracorporeal therapy machines.

Due to various causes, a person's renal system may fail. Renal failure produces several physiological derangements. It is no longer possible to balance water and minerals or to excrete daily metabolic load. Toxic end products of metabolism (urea, creatinine, uric acid, and others) may accumulate in blood and tissue.

Kidney failure and reduced kidney function have been treated with dialysis. Dialysis removes waste, toxins and excess water from the body that normal functioning kidneys would otherwise remove. Dialysis treatment for replacement of kidney functions is critical to many people because the treatment is life saving.

One type of kidney failure therapy is Hemodialysis ("HD"), which in general uses diffusion to remove waste products from a patient's blood. A diffusive gradient occurs across the semi-permeable dialyzer between the blood and an electrolyte solution called dialysate or dialysis fluid to cause diffusion.

Hemofiltration ("HF") is an alternative renal replacement therapy that relies on a convective transport of toxins from the patient's blood. HF is accomplished by adding substitution or replacement fluid to the extracorporeal circuit during treatment (typically ten to ninety liters of such fluid). The substitution fluid and the fluid accumulated by the patient in between treatments is ultrafiltered over the course of the HF treatment, providing a convective transport mechanism that is particularly beneficial in removing middle and large molecules (in hemodialysis there is a small amount of waste removed along with the fluid gained between dialysis sessions, however, the solute drag from the removal of that ultrafiltrate is not enough to provide convective clearance).

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Most HD (HF, HDF) treatments occur in centers. A trend towards home hemodialysis ("HHD") exists today in part because HHD may be performed daily, offering therapeutic benefits over in-center hemodialysis treatments, which occur typically twice a week or three times a week. Studies have shown that more frequent treatments remove more toxins and waste products than a patient receiving less frequent but perhaps longer treatments. A patient receiving more frequent treatments does not experience as much of a down cycle as does an in-center patient, who has built-up two or three days worth of toxins prior to a treatment. In certain areas, the closest dialysis center may be many miles from the patient's home causing door-to-door treatment time to consume a large portion of the day. A HHD treatment may take place overnight or during the day while the patient relaxes, works or is otherwise productive.

In any of the above modalities, it may be necessary to perform a disinfection sequence to clean the associated machine for a next treatment and to attempt to preserve the microbiological quality of filters that are relied upon to filter dialysis fluid so that it may be used safely to treat the patient. HF and HDF machines in particular may use one or more filters to filter replacement fluid that is delivered directly to one or both of the arterial and venous blood lines.

Many disinfecting fluids, may cause ageing of various materials and therefore may be harmful to metal and plastic components if left to contact the components for a prolonged period of time. Additionally, some disinfecting fluids leave a sticky residue when dried, which may be detrimental to the function of certain fluid components, such as medical fluid pumps. Still further, it has been shown in studies (e.g., https://www.researchgate.net/publication/12579423) testing the microbiological quality of substitution fluids that bacteria have been found despite attempts made to sterilize the fluid.

Improved disinfection systems and corresponding methods balancing the need to disinfect while mitigating certain drawbacks of the disinfecting fluid are needed accordingly.

SUMMARY

The examples described herein disclose automated systems and methods applicable in various embodiments to blood purification systems using a non-disposable fluid path for the treatment of blood, including but not limited too: Leukapheresis, LDL apheresis, therapeutic plasm exchange, hemodialysis ("HD"), hemofiltration ("HF") hemodiafiltration ("HDF"), continuous renal replacement therapy ("CRRT"), liver dialysis systems and possibly respiratory dialysis systems. Any of the extracorporeal therapies may require that the blood circuit include one or more filter with the intent to remove various components from a patient's blood.

The present disclosure includes a system and method for disinfecting desired locations and components within a dialysis machine (or other machine containing one or more treatment fluid purifying filter) over prolonged periods of time to ensure that the disinfected components are thoroughly disinfected. In particular, filters or ultrafilters used to purify dialysis fluid for treatment are subject to the prolonged disinfection in one embodiment. Other components, such as certain types of pumps that may have adverse reactions due to the prolonged disinfection, are prevented from seeing prolonged contact with the disinfecting fluid.

In one embodiment, the dialysis machine includes a dialysis fluid circuit that prepares fresh dialysis fluid, delivers the fresh dialysis fluid to a dialysis fluid side of a dialyzer, removes used dialysis fluid from the dialyzer and sends the used dialysis fluid to drain. The dialysis machine accepts a blood set and provides a blood pump to remove blood from a patient, pump the blood through a blood side of the dialyzer, removing waste and toxins from the blood, and return the blood to the patient. A separate pump is provided to deliver replacement fluid directly to one or more blood line of the blood set to further remove waste and toxins. A first filter or ultrafilter may be provided to purify the dialysis fluid delivered to the dialyzer, while a second filter or ultrafilter may be provided to further purify the purified dialysis fluid outputted from the first filter or ultrafilter.

In an embodiment, at the end of treatment, the dialysis machine performs a standard disinfection routine that disinfects all portions of the dialysis fluid circuit. The standard disinfection routine may use chemical and/or heat disinfection. At the end of the standard disinfection, any remaining disinfection fluid is flushed to drain using purified water in one embodiment, so that the dialysis fluid circuit is thereafter filled with purified water. In an alternative embodiment, the standard disinfection fluid may be maintained or held around and between the ultrafilters and flushed everywhere else to drain. In either scenario, a disinfecting fluid of the present disclosure, such as citric acid, is then introduced into the dialysis fluid circuit in a volume (dose) sufficient to reach and fill each of one or more, e.g., two, filters or ultrafilters. Next, purified water is used to push the dose of disinfecting fluid, e.g., citric acid, so that it fills both filters but is pushed past components sensitive to prolonged exposure to the disinfecting fluid, e.g., a fresh dialysis fluid pump, which may be a gear pump.

The selectively deployed disinfecting fluid is left to disinfect the filters for a prolonged period of time, e.g., multiple hours, such as ten or twelve hours. The next day for example, when preparing the machine for the first of perhaps multiple treatments performed during that day, the selectively deployed disinfecting fluid is pushed to drain, e.g., using purified water.

In light of the disclosure herein and without limiting the disclosure in any way, in a first aspect of the present disclosure, which may be combined with any other aspect listed herein unless specified otherwise, an extracorporeal therapy system includes: a dialysis fluid circuit including dialysis fluid preparation structure configured to prepare a dialysis fluid for an extracorporeal therapy treatment, the dialysis fluid circuit including a fresh dialysis fluid pump, a used dialysis fluid pump, and at least one filter for purifying the dialysis fluid; a blood circuit including a blood filter for use during the extracorporeal therapy treatment; a blood pump operable to pump blood through the blood circuit and blood filter; a source of disinfecting fluid; and a control unit operable with the dialysis fluid preparation structure and the blood pump, the control unit programmed to cause the disinfecting fluid to be delivered to and located for a duration of time at an area of the dialysis fluid circuit having the at least one purifying filter, and wherein during the duration the disinfecting fluid is precluded from contacting at least the fresh dialysis fluid pump.

In a second aspect of the present disclosure, which may be combined with any other aspect listed herein unless specified otherwise, the duration of time includes multiple hours.

In a third aspect of the present disclosure, which may be combined with any other aspect listed herein unless specified otherwise, the area having the disinfecting fluid is located between valves located upstream and downstream from the at least one purifying filter.

In a fourth aspect of the present disclosure, which may be combined with any other aspect listed herein unless specified otherwise, the area having the disinfecting fluid includes additional disinfecting fluid outside of at least one of the purifying filter to ensure that the area covers the at least one purifying filter.

In a fifth aspect of the present disclosure, which may be combined with any other aspect listed herein unless specified otherwise, wherein the area having the disinfecting fluid is located between the fresh dialysis fluid pump located upstream of the at least one purifying filter and a valve located downstream of the at least one purifying filter.

In a sixth aspect of the present disclosure, which may be combined with any other aspect listed herein unless specified otherwise, the extracorporeal therapy system includes a sensor operable with the dialysis fluid circuit, and wherein the control unit is programmed to detect a change in at least one signal from the sensor indicating that enough disinfecting fluid to fully fill the at least one purifying filter has entered the dialysis fluid circuit.

In a seventh aspect of the present disclosure, which may be combined with any other aspect listed herein unless specified otherwise, the control unit is programmed to cause a pump of the dialysis fluid circuit to be actuated for a number of pump strokes sufficient to expect that enough disinfecting fluid to fully fill the at least one purifying filter has entered the dialysis fluid circuit.

In an eighth aspect of the present disclosure, which may be combined with any other aspect listed herein unless specified otherwise, the extracorporeal therapy system includes a sensor operable with the dialysis fluid circuit, and wherein the control unit is programmed to detect a change in at least one signal from the sensor to determine that the disinfecting fluid has been brought to the area of the dialysis fluid circuit including the at least one purifying filter.

In a ninth aspect of the present disclosure, which may be combined with any other aspect listed herein unless specified otherwise, the control unit is programmed to cause a pump of the dialysis fluid circuit to be actuated for a number of pump strokes sufficient to expect that the disinfecting fluid has been brought to the area of the dialysis fluid circuit including the at least one purifying filter.

In a tenth aspect of the present disclosure, which may be combined with any other aspect listed herein unless specified otherwise, the control unit is programmed to cause a pump to backfill the dialysis fluid circuit to push the disinfecting fluid to reach the area of the dialysis fluid circuit including the at least one purifying filter.

In an eleventh aspect of the present disclosure, which may be combined with the tenth aspect in combination with any other aspect listed herein unless specified otherwise, the fresh dialysis fluid pump is thereafter contacted at least substantially with purified water during the duration of time.

In a twelfth aspect of the present disclosure, which may be combined with any other aspect listed herein unless specified otherwise, the disinfecting fluid is brought into contact with both pre- and post-sides of a plurality of membranes of the at least one purifying filter.

In a thirteenth aspect of the present disclosure, which may be combined with any other aspect listed herein unless specified otherwise, the disinfecting fluid includes citric acid.

In a fourteenth aspect of the present disclosure, which may be combined with any other aspect listed herein unless specified otherwise, an extracorporeal therapy system includes: a dialysis fluid circuit including dialysis fluid preparation structure configured to prepare a dialysis fluid for an extracorporeal therapy treatment, the dialysis fluid circuit including a fresh dialysis fluid pump, a used dialysis fluid pump, and at least one filter for purifying the dialysis fluid; a blood circuit including a blood filter for use during the extracorporeal therapy treatment; a source of disinfecting fluid; and a control unit operable with the dialysis fluid preparation structure, the control unit programmed to cause (i) a dose of disinfecting fluid sufficient to fill the at least one purifying filter to enter the dialysis fluid circuit and (ii) purified water to push the dose past at least one component of the dialysis fluid circuit for which it is desired to be free of the disinfecting fluid, so as to deliver the dose to and locate the dose for a duration of time at an area of the dialysis fluid circuit having the at least one purifying filter.

In a fifteenth aspect of the present disclosure, which may be combined with the fourteenth aspect in combination with any other aspect listed herein unless specified otherwise, the control unit is programmed to cause a pump of the dialysis fluid preparation structure to perform (i) and (ii).

In a sixteenth aspect of the present disclosure, which may be combined with the fourteenth aspect in combination with any other aspect listed herein unless specified otherwise, the control unit is programmed to use a predetermined number of pump strokes to perform at least one of (i) or (ii).

In a seventeenth aspect of the present disclosure, which may be combined with the fourteenth aspect in combination with any other aspect listed herein unless specified otherwise, the control unit is programmed to use sensor feedback to perform at least one of (i) or (ii).

In an eighteenth aspect of the present disclosure, which may be combined with any other aspect listed herein unless specified otherwise, an extracorporeal therapy disinfection method for a dialysis fluid circuit including dialysis fluid preparation structure configured to prepare a dialysis fluid for an extracorporeal therapy treatment, the dialysis fluid circuit including a fresh dialysis fluid pump, a used dialysis fluid pump, and at least one filter for purifying the dialysis fluid is provided, the method including: disinfecting at least substantially all of the dialysis fluid circuit using a first disinfecting fluid; rinsing the first disinfecting fluid to drain and filling at least substantially all of the dialysis fluid circuit with purified water; causing a dose of a disinfecting fluid sufficient to fill the at least one purifying filter to enter the dialysis fluid circuit; using purified water to push the dose past at least one component of the dialysis fluid circuit for which it is desired to be free of the second disinfecting fluid, so as to deliver the dose to and locate the dose at an area of the dialysis fluid circuit having the at least one purifying filter; and rinsing the second disinfecting fluid to drain.

In a nineteenth aspect of the present disclosure, which may be combined with the eighteenth aspect in combination with any other aspect listed herein unless specified otherwise, the first and second disinfecting fluids are different fluids.

In a twentieth aspect of the present disclosure, which may be combined with the eighteenth aspect in combination with any other aspect listed herein unless specified otherwise, the method includes locating the dose at the area of the dialysis fluid circuit having the at least one purifying filter for a prolonged duration of time.

In a twenty-first aspect of the present disclosure, which may be combined with the eighteenth aspect in combination with any other aspect listed herein unless specified otherwise, rinsing the first disinfecting fluid to drain includes leaving some of the first disinfecting fluid in contact with at least the membranes of the at least one purifying filter.

In a twenty-second aspect of the present disclosure, any of the structure and functionality disclosed in connection with FIGS. 1 to 4 may be combined with any of the other structure and functionality disclosed in connection with FIGS. 1 to 4.

In light of the present disclosure and the above aspects, it is therefore an advantage of the present disclosure to provide an extracorporeal therapy system and method having improved disinfection, and which maintains a bacteriostatic condition limiting any growth between treatments.

It is another advantage of the present disclosure to provide an extracorporeal therapy system and method having improved dialysis fluid circuit component retention.

It is a further advantage of the present disclosure to provide a relatively inexpensive system and method to improve dialysis fluid circuit component retention.

It is yet another advantage of the present disclosure to provide a system and method to improve dialysis fluid circuit component retention that requires little or no additional setup.

The advantages discussed herein may be found in one, or some, and perhaps not all of the embodiments disclosed herein. Additional features and advantages are described herein, and will be apparent from, the following Detailed Description and the figures.

DETAILED DESCRIPTION

The examples described herein are applicable to any medical fluid therapy system that delivers a medical fluid, such as blood, dialysis fluid, substitution fluid, purified or sterilized water, liquid concentrate, or an intravenous drug. The examples are particularly well suited for kidney failure therapies, such as all forms of hemodialysis ("HD"), plasmapheresis, hemofiltration ("HF") hemodiafiltration ("HDF"), continuous renal replacement therapy ("CRRT"), apheresis, autotransfusion, hemofiltration for sepsis, referred to herein collectively or generally individually as an extracorporeal therapy. Moreover, the systems and methods described herein may be used in clinical or home settings. Extracorporeal therapy system 10 in the examples below is described as a renal failure therapy system having a machine 12 that creates online dialysis fluid for treatment.

Figure 1:
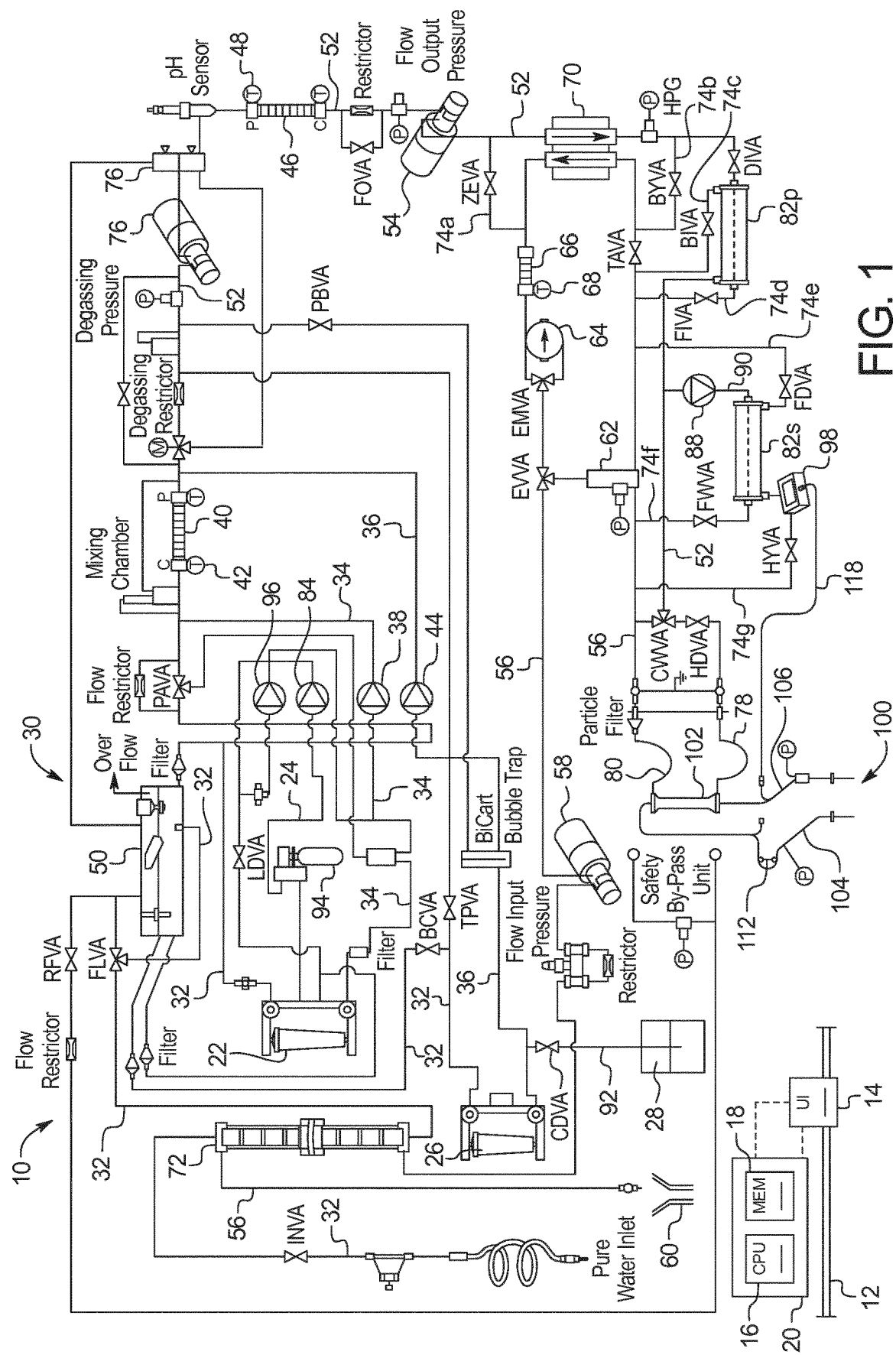
FIG. 1 is a schematic illustration of one example system of the present disclosure of the present disclosure employing localized disinfection.

Referring now to FIG. 1, one embodiment for a renal failure therapy system 10 employing a selective disinfection system and method for improving dialysis fluid circuit component retention and in particular the microbiological quality of the fluid in one or more ultrafilters is illustrated. System 10 includes a machine 12 having an enclosure or housing. The housing of machine 12 holds the contents of a dialysis fluid circuit 30 described in detail below. The housing of machine 12 also supports a user interface 14, which allows a nurse or other operator to interact with system 10. User interface 14 may have a monitor screen operable with a touch screen overlay, electromechanical buttons, e.g., membrane switches, or a combination of both. User interface 14 is in communication with at least one processor 16 and at least one memory 18. At least one processor 16 and at least one memory 18 also interact with, and where appropriate control, the pumps, valves and sensors described herein, e.g., those of dialysis fluid circuit 30. At least one processor 16 and at least one memory 18 are referred to collectively herein as a control unit 20. Control unit 20 includes electrical and/or signal lines leading to and/or from pumps, valves, sensors, the heater and the other electrical equipment of system 10 to receive information from those devices and/or to control those devices.

Dialysis fluid circuit 30 includes a purified water line 32, an A-concentrate line 34 and a bicarbonate B-concentrate line 36. Purified water line 32 receives purified water from a purified water device or source (e.g., an online source). The water may be purified using any one or more process, such as, reverse osmosis, carbon filtering, ultraviolet radiation, electrodeionization ("EDI"), and/or ultrafiltering.

An A-concentrate pump 38, such as a peristaltic or piston pump, pumps A-concentrate from an A-concentrate source (not illustrated) to mix with purified water from purified water line 32 via A-concentrate line 34, or (as illustrated) pumps purified water through purified water line 32 and a sodium cartridge 22 located along A-concentrate line 34 to mix with purified water from purified water line 32. Conductivity cell 40 measures the conductive effect of the A-concentrate on the purified water, sends a signal to control unit 20, which uses the signal to properly proportion the A-concentrate by controlling A-concentrate pump 38. The A-conductivity signal is temperature compensated via a reading from temperature sensor 42.

In the illustrated embodiment, a concentrate pump 84 under control of control unit 20, such as a peristaltic or piston pump, pumps a solution of electrolytes from a source 94 through an electrolyte cartridge line 24 to mix with sodium concentrate at A-concentrate line 34, when sodium cartridge 22 is used. A concentrate metering pump 96 under control of control unit 20 measures the flow from concentrate pump 84 through electrolyte cartridge line 24 to A-concentrate line 34 in the illustrated embodiment.

A B-concentrate pump 44, such as a peristaltic or piston pump, in the illustrated embodiment pumps B-concentrate from a liquid B-concentrate source (not illustrated) through B-concentrate line 36, or as illustrated purified water from purified water line 32 through a bicarbonate cartridge 26 located along B-concentrate line 36, into a mixture of purified water and A-concentrate leaving conductivity sensor 40. Conductivity cell 46 measures the conductive effect of the B-concentrate on the purified water/A-concentrate mixture, sends a signal to control unit 20, which uses the signal to properly proportion the B-concentrate by controlling B-concentrate pump 44. Conductivity cell 46 measures the conductivity of fully mixed fresh dialysis fluid. Conductivity cell 46 is also in communication with control unit 20 and temperature compensated via temperature sensor 48 (each conductivity cell may be temperature compensated).

A degassing pump (under control of control unit 20) and associated degassing chamber 76 are provided upstream of conductivity cell 46 in the illustrated embodiment to degas air from the fresh dialysis fluid. Also, in the illustrated embodiment, a source of disinfecting fluid 28, such as citric acid, is provided. Disinfecting fluid 28 may be connected via disinfecting fluid line 92 to B-concentrate line 36 as illustrated in FIG. 1.

FIG. 1 further illustrates that fully made fresh dialysis fluid is pumped through a fresh dialysis fluid line 52 via a fresh dialysis fluid pump 54 under control of control unit 20, such as a gear pump, which delivers fresh dialysis fluid for treatment to dialyzer 102. Control unit 20 controls fresh dialysis fluid pump 54 to deliver fresh dialysis fluid to the dialyzer at a specified flowrate. A used dialysis fluid line 56 via a used dialysis fluid pump 58 returns used dialysis fluid from dialyzer 102 to a drain 60. Control unit 20 controls used dialysis fluid pump 58 to pull used dialysis fluid from dialyzer 102 at a specified flowrate. An air separator 62 separates air from the used dialysis fluid line 56. A blood leak detector 64 communicating with control unit 20, e.g., an optical sensor, looks for blood in the drain line 56, indicating a leaking dialyzer 102.

Conductivity cell 66 measures the conductivity of used fluid flowing through used dialysis fluid line 56 and sends a signal to control unit 20. The conductivity signal of cell 66 is also temperature compensated via a reading from temperature sensor 68. A heat exchanger 72 in the illustrated embodiment recoups heat from the used dialysis fluid exiting dialysis fluid circuit 30 to drain 60, preheating the purified water traveling towards heating vessel 50 to conserve energy.

Dialysis circuit 30 includes an ultrafiltration ("UF") system 70. UF system 70 monitors the flowrate of fresh dialysis fluid flowing to dialyzer 102 (and/or as substitution fluid flowing directly to blood set 100) and used fluid flowing from dialyzer 102. UF system 70 may include fresh and used flow sensors, which send signals to control unit 20 indicative of the fresh and used dialysis fluid flowrates, respectively. Control unit 20 uses the signals to set used dialysis fluid pump 58 to pump faster than fresh dialysis fluid pump 54 by a predetermined amount to remove a prescribed amount of UF from the patient over the course of treatment.

FIG. 1 illustrates that system 10 may provide multiple fluid bypass lines extending from a fresh side of dialysis fluid circuit 30 to drain line 56. A first fluid bypass line 74a extends from a pre-UF system 70 location in fresh dialysis fluid line 52 to drain line 56. A second fluid bypass line 74b extends from a post-UF system 70 location in fresh dialysis fluid line 52 to drain line 56. A third fluid bypass line 74c extends from a secondary port of a post-side of primary ultrafilter 82p to drain line 56. A fourth bypass line 74d extends from an outlet port of a pre-side of primary ultrafilter 82p to drain line 56. A fifth fluid bypass line 74e extends from a secondary port of a post-side of substitution fluid ultrafilter 82s to drain line 56. A sixth bypass line 74f extends from an outlet port of a pre-side of secondary ultrafilter 82s to drain line 56. A seventh bypass line 74g extends from an outlet port of a post-side of secondary ultrafilter 82s to drain line 56. Each of the fluid bypass lines (may be more or less than illustrated) allows fresh dialysis fluid or substitution fluid to flow from the fresh dialysis fluid line 52 to used dialysis fluid line 56 without contacting dialyzer 102.

Each of bypass lines 74a to 74g is also selectively opened or closed via a unique bypass valve, e.g., an electrically operated solenoid valve under control of control unit 20. In the illustrated embodiment, bypass line 74a is selectively opened or closed via bypass valve ZEVA, bypass line 74b is selectively opened or closed via bypass valve BYVA, bypass line 74c is selectively opened or closed via bypass valve BIVA, bypass line 74d is selectively opened or closed via bypass valve FIVA, bypass line 74e is selectively opened or closed via bypass valve FDVA, bypass line 74f is selectively opened or closed via bypass valve FWVA, while bypass line 74g is selectively opened or closed via bypass valve HYVA.

In addition to bypass valves ZEVA, BYVA, BIVA, FIVA, FDVA, FWVA and HYVA, dialysis fluid circuit 30 also includes a three-port, two-way valve CWVA to either flow to valve HDVA or be shunted to drain line 56. Valve HDVA is the final shut-off valve in fresh dialysis fluid line 52 before dialyzer 102. Other valves of dialysis fluid circuit 30, such as purified water inlet valve INVA, disinfecting fluid valve CDVA located between disinfecting fluid source 28 and B-concentrate line 36, and ultrafilter upstream valve DIVA, are likewise labeled with four capitalized letters ending in "VA". Any one or more or all of those valves may likewise be electrically operated solenoid valves under control of control unit 20.

A fresh dialysis fluid tube 78 extends from machine 12 and carries fresh dialysis fluid from fresh dialysis fluid line 52 to dialyzer 102. Fresh dialysis fluid line 52 extends through the pre- and post-sides of primary ultrafilter 82*p*, which further purifies the fresh dialysis fluid for treatment. A used dialysis fluid tube 80 also extends from machine 12 and carries used dialysis fluid from dialyzer 102 to used dialysis fluid line 56.

As discussed, a primary ultrafilter 82*p* is provided to further purify the fresh dialysis fluid before being delivered via dialysis fluid line 52 and fresh dialysis fluid tube 78 to dialyzer 102. Additionally, a substitution ultrafilter 82*s* may be provided to further purify the fresh dialysis fluid from fresh dialysis fluid line 52 purified by primary ultrafilter 82*p* to the point where the fluid exiting substitution ultrafilter 82*s* may be used as a substitution fluid to perform from pre- and/or post-dilution hemofiltration or hemodiafiltration, in which the substitution fluid is delivered directly to one or both of arterial line 104 and/or venous line 106 of blood set 100 (illustrated in detail in FIG. 2). In the illustrated embodiment, a substitution fluid pump 88 under control of control unit 20 is placed in a substitution fluid line 90 leading from fresh dialysis fluid line 52 to a substitution port 98. Substitution fluid pump 88 is in one embodiment specifically designed to withstand acidic or corrosive solutions over long periods of time, e.g., overnight while machine 12 is not in use. One suitable type of pump for substitution fluid pump 88 is a peristaltic pump, in which the solution only contacts an inside of a tube operating with a peristaltic pump head.

It should be appreciated that dialysis fluid circuit 30 as illustrated is simplified and may include other structure (e.g., more valves and additional concentrate options) and functionality not illustrated. Also, dialysis fluid circuit 30 illustrates examples of a hemodialysis ("HD"), hemofiltration ("HF") and hemodiafiltration ("HDF") pathways. In particular, flow only from primary ultrafilter 82*p*, though the distal portion of dialysis fluid line 52, to dialyzer 102 performs HD. Flow only from substitution fluid ultrafilter 82*s* (via primary ultrafilter 82*p*), through substitution line 118 to arterial line 104 and/or venous line 106 performs HF. Flow from both from primary ultrafilter 82*p*, though the distal portion of dialysis fluid line 52, to dialyzer 102 in combination with flow from substitution fluid ultrafilter 82*s* (via primary ultrafilter 82*p*), though substitution line 118 to arterial line and/or venous line 106 performs HDF.

Figure 2:
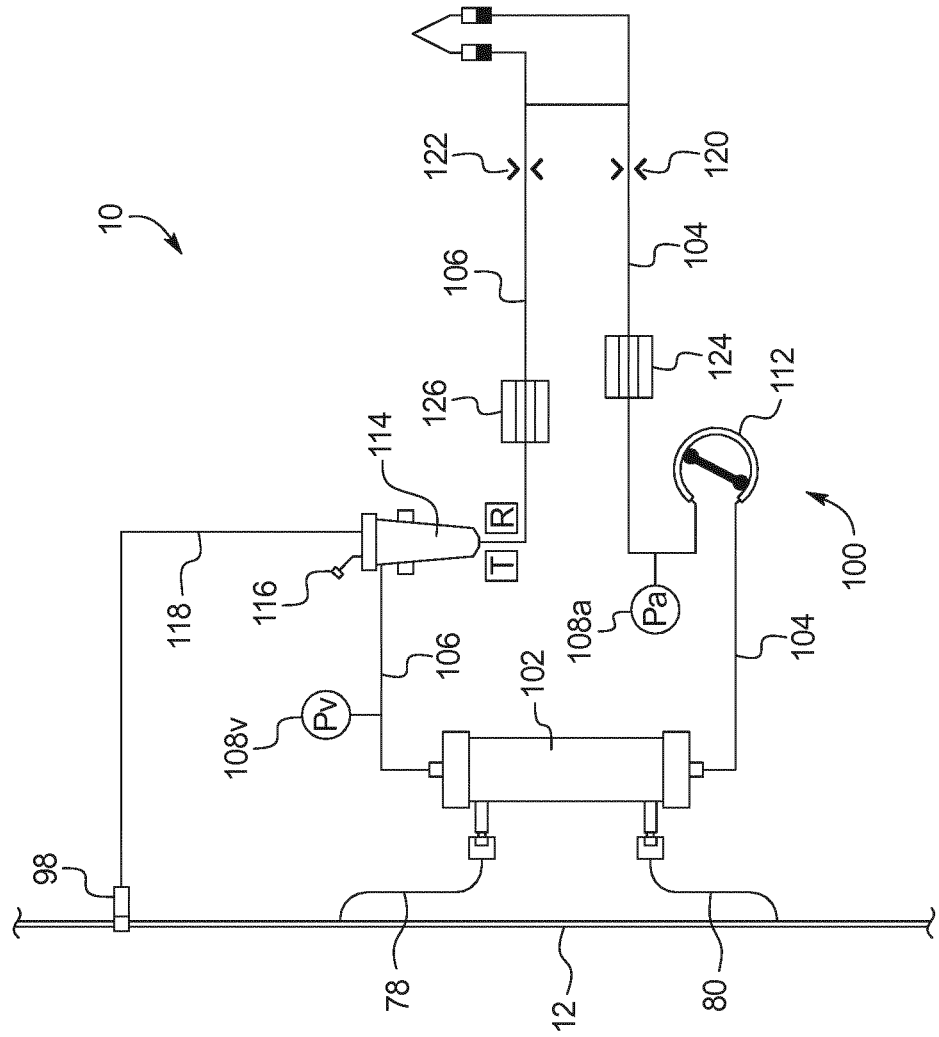
FIG. 2 is a schematic illustration of one example blood set and circuit that may be used with the system of FIG. 1.

FIG. 2 illustrates in more detail one embodiment of a blood circuit or set 100 that may be used with machine 12 of system 10. Blood circuit or set 100 includes a dialyzer 102 having many hollow fiber semi-permeable membranes, which separate dialyzer 102 into a blood compartment and a dialysis fluid compartment. The dialysis fluid compartment during treatment is placed in fluid communication with a distal end of fresh dialysis fluid tube 78 and a distal end of used dialysis fluid tube 80. For HF and HDF, a separate substitution tube 118 is placed during treatment in fluid communication with one or both of arterial line 104 and/or venous line 106, e.g., at venous drip chamber 114 as illustrated in FIG. 2.

An arterial pressure connector 108*a* may be placed upstream of blood pump 112 (such as a peristaltic or volumetric membrane pump under control of control unit 20), while venous line 106 includes a pressure connector 108*v*. Pressure connectors 108*a* and 108*v* operate with blood pressure sensors (not illustrated) mounted onto the housing of machine 12, which send arterial and venous pressure signals, respectively, to control unit 20. Venous line 106 includes a venous drip chamber 114, which removes air from the patient's blood before the blood is returned to the patient, and which may be provided with a hydrophobic vent 116.

In the illustrated embodiment, arterial line 104 of blood circuit or set 100 is operated by blood pump 112, which under control of control unit 20 pumps blood and other fluids as needed at a desired flowrate. System 10 also provides multiple blood side electronic devices that send signals to and/or receive commands from control unit 20. For example, control unit 20 commands clamps, such as arterial line clamp 120 and venous line clamp 122, to selectively open or close arterial line 104 and/or venous line 106, respectively. A blood volume sensor ("BVS") 124 outputting to control unit 20 may be located along arterial blood line 104 upstream of blood pump 112. An air detector 126 may be provided to look for air in venous blood line 106. As with dialysis fluid circuit 30, blood set or circuit 100 is simplified in FIG. 1 for ease of illustration and may include additional structure and functionality. The distal ends of arterial and venous lines 104 and 106 may be connected together during disinfection as illustrated in FIG. 2. Or, blood set 100 may be removed during disinfection, in which case fresh dialysis fluid tube 78 and used dialysis fluid tube 80 may be connected together or plugged into machine 12 to form a loop with dialysis fluid circuit 30.

Figure 3:
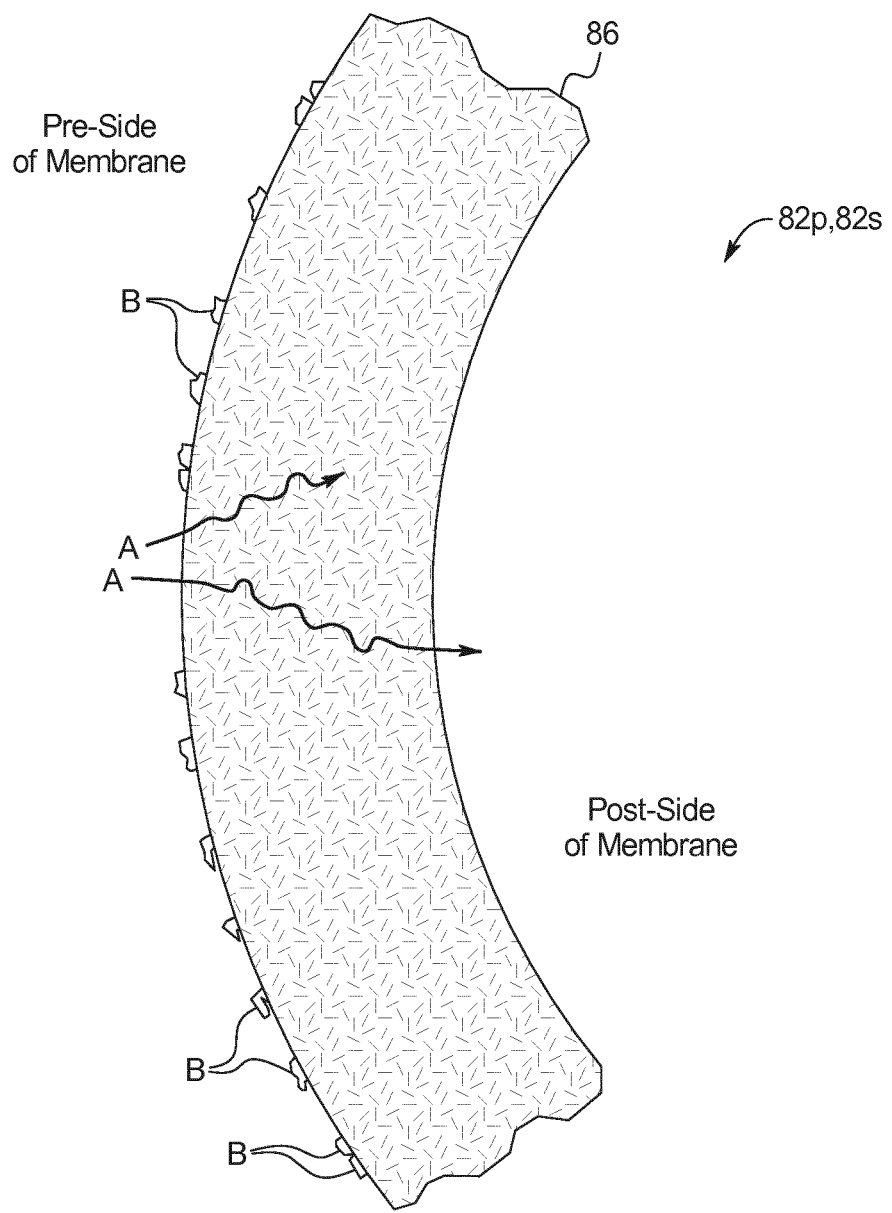
FIG. 3 is a cross-sectional view of a section of a purifying filter membrane illustrating flow through the section and potential build-up of bacteria.

FIG. 3 illustrates one embodiment of a cross-section taken through a section of one of the many membranes 86 located within primary and substitution fluid ultrafilters 82*p* and 82*s*. Suitable ultrafilters 82*p* and 82*s* include U 8000 S, U 9000 and Diaclear™ Ultrafilters provided by the assignee of the present disclosure. As illustrated by arrows A in FIG. 3, flow of fluid is in one embodiment from the outside of membrane 86 (pre-side of ultrafilters 82*p* and 82*s*) to the inside of membrane 86 (post-side of ultrafilters 82*p* and 82*s*). In an alternative embodiment, flow through membrane 86 is from the inside of the membranes to the outside of the membranes. Bacterial growth B may occur especially on the pre-sides of the membranes 86 (pre-sides of ultrafilters 82*p* and 82*s*). Unlike dialyzers 102, which contact the patient's blood and are therefore normally single use, ultrafilters 82*p* and 82*s* are typically used for long periods of time, e.g., months. In the system and method of the present disclosure, a disinfecting solution, such as an acid solution, e.g., citric acid, is used to contact and inactivate bacteria B. Other suitable acid solutions include acetic acid, sodium diacetate acid, lactate which may be obtained from the A-concentrate, and combinations and derivatives thereof.

In particular, diluted (e.g., two to three percent) citric acid has a pH of about 2.2 to 2.5. Most microorganisms grow best at pH values around 7.0, while only a few grow at a pH below 4.0. Even yeasts and molds that are more tolerant to low pH are unlikely to grow in an environment having a pH of 3. Thus, citric acid, which is an organic acid that is a natural preservative/conservative is a good candidate to use to inactivate and/or stop the growth of bacteria B illustrated in FIG. 3 forming on membranes 86 of ultrafilters 82*p* and 82*s*. But citric acid is highly corrosive and becomes sticky when drying, which may be harmful to certain areas of machine 12, e.g., its pumps 38, 44, 54, 84 and 96. It is accordingly contemplated to deliver and let sit for prolonged periods of time, e.g., overnight and on the order of ten to fifteen hours, the citric acid solution to only those areas of dialysis fluid circuit 30 that need disinfection the most, e.g., to ultrafilters 82*p* and 82*s* and surrounding tubing, and perhaps specifically to the pre-sides of ultrafilters 82*p* and 82*s* (e.g., the outsides of membranes 86).

Example Disinfecting and Bacteriostatic Fluid Sequence

Figure 4:
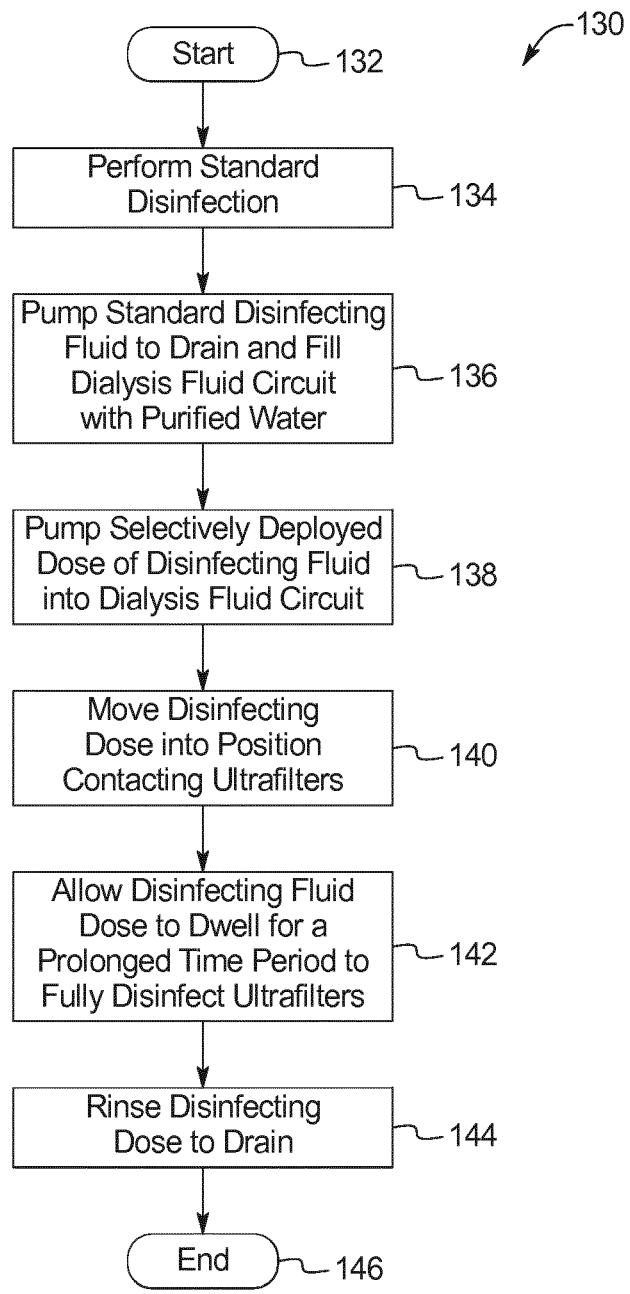
FIG. 4 is a schematic flowchart illustrating one example disinfecting method of the present disclosure, which may be performed using the system of FIGS. 1 and 2.

Viewing FIG. 1 and referring additionally to method 130 of FIG. 4, which begins at oval 132, in one embodiment, after a standard disinfection of machine 12 at block 134 (e.g., chemically and/or via heat), and at the end of the day when there are no additional treatments, control unit 20 at block 136 opens purified water inlet valve INVA to cause (i) the standard disinfection fluid residing within dialysis fluid circuit 30 to be pumped, e.g., via dialysis fluid pumps 54 and 58 (and with any one or more or all of bypass lines 74*a* to 74*g* open) to drain 60, and (ii) dialysis fluid circuit 30 to be filled with purified water from the purified via water inlet line 32 and water inlet source (e.g., an online source). In an alternative embodiment during rinse using purified water, valves DIVA, BIVA and FIVA for primary ultrafilter 82*p* may be closed, while valves FDVA, FWVA and HYVA for secondary ultrafilter 82*p* are closed, so that the standard disinfection fluid is maintained around the membranes 86 of the ultrafilters during the rinse. Here, adjacent bypass lines, such as one or both bypass lines 74*a* and 74*b* may be opened to allow the standard disinfection fluid to flow from fresh dialysis fluid line 52 to used dialysis fluid line 56, to drain 60.

Next at block 138, with dialysis fluid circuit 30 filled with purified water, control unit 20 causes purified water inlet valve INVA to close, disinfecting fluid valve CDVA to open, and B-concentrate pump 44 to pull and push enough disinfecting fluid from disinfecting fluid source 28 to fill ultrafilters 82*p* and 82*s* and to reach at least from ultrafilter upstream valve DIVA (i) to valve FIVA to fully wet and fill primary ultrafilter 82*p* with disinfecting fluid from source 28 and (ii) to valves CWVA, FWVA, FDVA and HYVA to fully wet and fill substitution ultrafilter 82*s* with disinfecting fluid from source 28 (plus some additional disinfecting fluid knowing that the dose of disinfecting fluid at its ends will mix with purified water).

In one embodiment, the approximate volume of disinfecting fluid that each stroke of B-concentrate pump 44 (e.g., a peristaltic or gear pump) pumps is known as well as the total volume of disinfecting fluid needed for (i) and (ii) in the previous paragraph to fully wet and fill primary ultrafilter 82*p* and secondary ultrafilter 82*s*. The total volume needed is divided by the volume per stroke, and the resulting number of strokes plus some additional strokes for assurance are programmed into control unit 20 to be used at block 138.

In another embodiment, conductivity cell 46 is used to meter a desired amount of disinfecting fluid from source 28 into dialysis fluid circuit 30. Here, assuming the total volume of disinfecting fluid needed for (i) and (ii) above to fully wet and fill primary ultrafilter 82*p* and secondary ultrafilter 82*s* is less than the volume of the combined flowpaths within dialysis fluid circuit 30 extending from disinfecting fluid source 28, through disinfecting fluid line 92, through B-concentrate line 36 and through a portion of fresh dialysis fluid line 52 to conductivity cell 46, then when the disinfecting fluid is sensed by conductivity cell 46, it is assured that enough disinfecting fluid resides within dialysis fluid circuit 30 to disinfect primary ultrafilter 82*p* and secondary ultrafilter 82*s* properly. In an embodiment, control unit 20 is programmed to look for a conductivity reading corresponding to, for example, ninety percent to one-hundred percent disinfecting fluid versus a reading for purified water, and to not react at an initial change in conductivity due to a mixture of disinfecting fluid and purified water.

At block 140, after performing any of the embodiments for intaking the desired amount of disinfectant discussed above, control unit 20 causes disinfecting fluid valve CDVA to close, purified water inlet valve INVA to open, and B-concentrate pump 44 to pull and push enough purified water from water inlet line 32 connected to a water source to move the dose of disinfecting fluid into a proper location such that it fully wets and fills primary ultrafilter 82*p* and secondary ultrafilter 82*s*, while no longer contacting components that may be harmed due to prolonged contact with the disinfecting fluid, e.g., fresh dialysis fluid pump 54. Fresh dialysis fluid pump 54 may also need to be operated to move the dose of disinfecting fluid.

As with filling dialysis fluid circuit 30 with disinfecting fluid, moving the dose at block 140 may be performed by counting pump strokes, using conductivity sensors or a combination of both. Viewing FIG. 1, it may be desirable to move the trailing edge of the dose past UF system 70 to ensure that traces of the disinfecting fluid mixed with water have cleared fresh dialysis fluid pump 54. Thus in one embodiment, control unit 20 pumps a number of strokes of B-concentrate pump 44 that are expected to move the trailing end of the dose past UF system 70.

In another embodiment, control unit 20 opens bypass valve ZEVA to allow the moving dose of disinfecting fluid to be sensed at conductivity sensor 66, so that when the disinfecting fluid is no longer sensed at conductivity sensor 66, control unit 20 may stop B-concentrate pump 44 and close valve ZEVA. In a further embodiment, so as not to push too much disinfecting fluid down drain line 56 towards used dialysis fluid pump 58, control unit may actuate B-concentrate pump 44 for a certain amount of strokes or time for which it is expected that the trailing end of the disinfecting fluid dose is close to conductivity sensor 66, at which point control unit 20 opens bypass valve ZEVA to allow the moving dose of disinfecting fluid to be sensed at conductivity sensor 66, so that when the disinfecting fluid is no longer sensed at conductivity sensor 66, control unit 20 may stop B-concentrate pump 44 and close valve ZEVA.

Block 140 also includes control unit 20 opening appropriate valves to enable the disinfecting fluid to reach and fill primary ultrafilter 82*p* and secondary ultrafilter 82*s*, including opening valves DIVA, HYVA, CWVA (path to HDVA), HDVA and HYVA. Control unit 20 may also run substitution pump 88. Opening valves DIVA, HYVA, CWVA (path to HDVA), HDVA and HYVA and running substitution pump 88 enables disinfection fluid to reach and contact both the pre- and post-sides of membranes 86 illustrated in FIG. 4.

At block 142, after moving the dose of disinfecting fluid into a proper location, control unit 20 closes purified water inlet valve INVA, closes ultrafilter valves DIVA, HYVA, CWVA, HDVA and HYVA and stops B-concentrate pump 44, substitution pump 88 and fresh dialysis fluid pump 54 if operated, trapping the dose of disinfecting fluid in position to disinfect ultrafilter 82*p* and secondary ultrafilter 82*s*. Disinfecting fluid is caused to remain in the disinfecting location for a desired amount of time, e.g., multiple hours, such as ten to fifteen hours.

At block 144, e.g., at the beginning of the next day's round of treatments, control unit 20 opens purified water inlet valve INVA and all other valves desired to rinse dialysis fluid circuit 30 with purified water and send the disinfecting fluid from source 28 to drain.

At oval 146, method 146 ends.

ELEMENT NUMBER LISTING

10—system
12—machine
14—user interface
16—processor
18—memory
20—control unit
22—sodium cartridge
24—electrolyte cartridge line
26—bicarbonate cartridge
28—source of disinfecting fluid
30—dialysis fluid circuit
32—purified water line
34—A-concentrate line
36—B-concentrate line
38—A-concentrate pump
40—conductivity cell
42—temperature sensor for conductivity cell 40
44—B-concentrate pump
46—conductivity cell
48—temperature sensors for conductivity cell 46
50—heating vessel
52—fresh dialysis fluid line
54—fresh dialysis fluid pump
56—drain line
58—used dialysis fluid pump
60—drain
62—air separator
64—blood leak detector
66—conductivity cell
68—temperature sensor for conductivity cell 66
70—UF system
72—heat exchanger
74a—first fluid bypass line
74b—second fluid bypass line
74c—third fluid bypass line
74d—fourth fluid bypass line
74e—fifth bypass line
74f—sixth bypass line
74g—seventh bypass line
76—degassing pump and chamber
78—fresh dialysis fluid tube
80—used dialysis fluid tube
82p—primary ultrafilter
82s—substitution ultrafilter
84—concentrate pump
86—membranes of ultrafilters
88—substitution pump
90—substitution fluid line
92—disinfecting fluid line
94—source of electrolytes
96—concentrate pump
98—substitution port
100—blood set
102—dialyzer
104—arterial line
106—venous line
108a—arterial pressure connector
108v—venous pressure connector
112—blood pump
114—venous drip chamber
116—hydrophobic vent
118—substitution line
120—arterial line clamp
122—venous line clamp
124—blood volume sensor
126—air detector
130—method
132 to 146—method steps It should be understood that various changes and modifications to the presently preferred embodiments described herein will be apparent to those skilled in the art. Such changes and modifications may be made without departing from the spirit and scope of the present subject matter and without diminishing its intended advantages. It is therefore intended that such changes and modifications be covered by the appended claims.

The invention is claimed as follows:

1. An extracorporeal therapy system comprising:
a dialysis fluid circuit including a dialysis fluid preparation structure configured to prepare a dialysis fluid for an extracorporeal therapy treatment, the dialysis fluid circuit including a pump, at least one filter for purifying the dialysis fluid, and at least one component located upstream of the at least one filter;
a blood circuit including a blood filter for use during the extracorporeal therapy treatment;
a source of disinfecting fluid; and
a control unit operable with the dialysis fluid circuit and the dialysis fluid preparation structure, the control unit programmed to cause the pump of the dialysis fluid circuit to pump:
(i) a dose of disinfecting fluid into the dialysis fluid circuit, the dose being sufficient to fill the at least one purifying filter, and
(ii) purified water to push the dose past the at least one component so as to deliver the dose to and locate the dose for a duration of time at an area of the dialysis fluid circuit having the at least one purifying filter.

2. The extracorporeal therapy system of claim 1, wherein the dialysis fluid circuit further includes a fresh dialysis fluid pump and a used dialysis fluid pump, and wherein the at least one component of the dialysis fluid circuit for which it is desired to be free of the disinfecting fluid includes at least one of the fresh dialysis fluid pump and the used dialysis fluid pump.

3. The extracorporeal therapy system of claim 2, wherein the area having the disinfecting fluid is located between the fresh dialysis fluid pump, which is located upstream of the at least one purifying filter, and at least one valve, which is located downstream of the at least one purifying filter.

4. The extracorporeal therapy system of claim 2, wherein the area having the disinfecting fluid is located between valves placed upstream and downstream from the at least one purifying filter, and the control unit is programmed to close the valves located upstream and downstream from the at least one purifying filter to trap the dose of disinfecting fluid in position to disinfect the at least one purifying filter.

5. The extracorporeal therapy system of claim 4, wherein the fresh dialysis fluid pump is contacted at least substantially with purified water during the duration of time.

6. The extracorporeal therapy system of claim 1, wherein the duration of time is at least multiple hours.

7. The extracorporeal therapy system of claim 1, wherein the area having the disinfecting fluid is located between valves located upstream and downstream from the at least one purifying filter.

8. The extracorporeal therapy system of claim 1, wherein the area to which the disinfecting fluid is delivered includes a portion outside of the at least one purifying filter to ensure that the area covers the at least one purifying filter.

9. The extracorporeal therapy system of claim 1, which includes a sensor operable with the dialysis fluid circuit, and wherein the control unit is programmed to detect a change in at least one signal from the sensor indicating that enough disinfecting fluid to at least partially fill the at least one purifying filter has entered the dialysis fluid circuit.

10. The extracorporeal therapy system of claim 1, wherein the control unit is programmed to cause a pump of the dialysis fluid circuit to be actuated for a number of pump strokes sufficient to pump enough disinfecting fluid to at least partially fill the at least one purifying filter through the dialysis fluid circuit.

11. The extracorporeal therapy system of claim 1, which includes a sensor operable with the dialysis fluid circuit, and wherein the control unit is programmed to detect a change in at least one signal from the sensor to determine that the disinfecting fluid has been brought to the area of the dialysis fluid circuit including the at least one purifying filter.

12. The extracorporeal therapy system of claim 1, wherein the control unit is programmed to cause a pump of the dialysis fluid circuit to be actuated for a number of pump strokes so that the disinfecting fluid is brought to the area of the dialysis fluid circuit including the at least one purifying filter.

13. The extracorporeal therapy system of claim 1, wherein the control unit is programmed to cause a pump to backfill the dialysis fluid circuit to move the disinfecting fluid to reach the area of the dialysis fluid circuit including the at least one purifying filter.

14. The extracorporeal therapy system of claim 13, wherein the pump is thereafter flushed with purified water during the duration of time.

15. The extracorporeal therapy system of claim 1, wherein the disinfecting fluid is brought into contact with both pre- and post-sides of a plurality of membranes of the at least one purifying filter.

16. The extracorporeal therapy system of claim 1, wherein the disinfecting fluid includes citric acid.

17. The extracorporeal therapy system of claim 1, which includes a blood pump operable with the control unit to pump blood through the blood circuit and the blood filter.

18. The extracorporeal therapy system of claim 1, wherein the dialysis fluid preparation structure comprises the pump of to perform (i) and (ii).

19. An extracorporeal therapy machine comprising:
a dialysis fluid circuit including a dialysis fluid preparation structure with a pump, the dialysis fluid preparation structure being configured to prepare a dialysis fluid for an extracorporeal therapy treatment, the dialysis fluid circuit including a fresh dialysis fluid pump, a used dialysis fluid pump, and at least one filter for purifying the dialysis fluid;
valves located upstream and downstream from the at least one purifying filter;
a source of a disinfecting fluid;
a blood circuit including a blood filter for use during the extracorporeal therapy treatment a blood pump for pumping blood through the blood filter during the extracorporeal therapy treatment; and
a control unit operable with the dialysis fluid circuit and the dialysis fluid preparation structure, the control unit programmed to:
cause at least one of the pump, the fresh dialysis fluid pump, or the used dialysis fluid pump to pump the disinfecting fluid from the source of disinfecting fluid to an area of the dialysis fluid circuit having the at least one purifying filter,
stop the at least one of the pump, the fresh dialysis fluid pump, or the used dialysis fluid pump to cause the disinfecting fluid to remain for a duration of time at the area of the dialysis fluid circuit having the at least one purifying filter, the delivered disinfecting fluid being a dose of disinfecting fluid sufficient to fill the at least one purifying filter, the area being located between the valves, and
close the valves located upstream and downstream from the at least one purifying filter to trap the dose of disinfecting fluid in position to disinfect the at least one purifying filter,
wherein during the duration of time the disinfecting fluid is precluded from contacting at least one of the fresh dialysis fluid pump or the used dialysis fluid pump for which it is desired to be free of the disinfecting fluid.

20. An extracorporeal therapy disinfection method for a dialysis fluid circuit including dialysis fluid preparation structure configured to prepare a dialysis fluid for an extracorporeal therapy treatment, the dialysis fluid circuit including at least one filter for purifying the dialysis fluid, the method comprising:
disinfecting at least substantially all of the dialysis fluid circuit using a first disinfecting fluid;
rinsing the first disinfecting fluid to drain and filling at least substantially all of the dialysis fluid circuit with purified water;
causing a dose of a second disinfecting fluid sufficient to fill the at least one purifying filter to enter the dialysis fluid circuit;
using purified water to push the dose past at least one component of the dialysis fluid circuit for which it is desired to be free of the second disinfecting fluid, so as to deliver the dose to, and locate the dose at, an area of the dialysis fluid circuit having the at least one purifying filter; and
rinsing the second disinfecting fluid to drain.

21. The extracorporeal therapy disinfection method of claim 20, wherein the first and second disinfecting fluids are different fluids.

22. The extracorporeal therapy disinfection method of claim 20, which includes locating the dose at the area of the dialysis fluid circuit having the at least one purifying filter for a prolonged duration of time.

23. The extracorporeal therapy disinfection method of claim 20, wherein the at least one purifying filter includes a plurality of membranes, and wherein rinsing the first disinfecting fluid to drain includes leaving an amount of the first disinfecting fluid in contact with at least the membranes of the at least one purifying filter.

24. An extracorporeal therapy system including:
a dialysis fluid circuit including a dialysis fluid preparation structure configured to prepare a dialysis fluid for an extracorporeal therapy treatment, the dialysis fluid circuit including a pump, at least one filter for purifying the dialysis fluid, a source of a first disinfecting fluid and a source of a second disinfecting fluid, and at least one component fluidly coupled to the at least one filter; and
a control unit operable with the dialysis fluid circuit, the control unit being programmed to:
cause the pump to move the first disinfecting fluid to disinfect at least substantially all of the dialysis fluid circuit,
cause the pump to rinse the first disinfecting fluid to drain and fill at least substantially all of the dialysis fluid circuit with purified water, cause the pump to move a dose of the second disinfecting fluid to the dialysis fluid circuit, the dose being sufficient to fill the at least one purifying filter,
cause the pump to move purified water to push the dose past at least one component of the dialysis fluid circuit for which it is desired to be free of the second disinfecting fluid, so as to deliver the dose to, and locate the dose at, an area of the dialysis fluid circuit having the at least one purifying filter, and
cause the pump to rinse the second disinfecting fluid to drain.

* * * * *